US012618685B2

(12) United States Patent
Lang et al.

(10) Patent No.: US 12,618,685 B2
(45) Date of Patent: *May 5, 2026

(54) SENTIMENT-BASED NAVIGATION

(71) Applicant: AT&T Intellectual Property I, L.P., Atlanta, GA (US)

(72) Inventors: Howard Lang, Wayside, NJ (US); Joseph Soryal, Glendale, NY (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 29 days.

This patent is subject to a terminal disclaimer.

(21) Appl. No.: 18/754,802

(22) Filed: Jun. 26, 2024

(65) Prior Publication Data

US 2024/0344840 A1     Oct. 17, 2024

Related U.S. Application Data

(63) Continuation of application No. 17/307,465, filed on May 4, 2021, now Pat. No. 12,055,404.

(51) Int. Cl.
| | |
|---|---|
| *G01C 21/36* | (2006.01) |
| *G10L 25/63* | (2013.01) |
| *A61B 5/0205* | (2006.01) |
| *A61B 5/024* | (2006.01) |
| *G06F 3/16* | (2006.01) |

(Continued)

(52) U.S. Cl.
CPC ..... *G01C 21/3617* (2013.01); *G01C 21/3608* (2013.01); *G01C 21/362* (2013.01); *G01C 21/3641* (2013.01); *G10L 25/63* (2013.01); *A61B 5/02055* (2013.01); *A61B 5/024* (2013.01); *B60W 2540/21* (2020.02); *B60W*

*2540/22* (2013.01); *B60W 2540/221* (2020.02); *B60W 2540/229* (2020.02); *G06F 3/167* (2013.01); *G06F 2203/011* (2013.01); *G06V 20/597* (2022.01); *G08B 21/06* (2013.01)

(58) Field of Classification Search
CPC ............ G01C 21/3617; G01C 21/3608; G01C 21/362; G01C 21/3641; G10L 25/63
See application file for complete search history.

(56) References Cited

U.S. PATENT DOCUMENTS

| | | |
|---|---|---|
| 8,364,514 B2 | 1/2013 | Macbeth et al. |
| 2012/0150430 A1 | 6/2012 | French et al. |

(Continued)

OTHER PUBLICATIONS

Jung , et al., "Highly sensitive driver health condition monitoring system using nonintrusive active electrodes", Sensors and Actuators B 171-172, 2012, 8 pages.

(Continued)

*Primary Examiner* — Aryan E Weisenfeld
(74) *Attorney, Agent, or Firm* — Guntin & Gust, PLC; Erik Boyd

(57) ABSTRACT

Sentiment-based navigation is provided herein. A method can include extracting features of sensor data captured by a sensor associated with a vehicle, wherein the sensor data is representative of a subject selected from a group of subjects comprising an occupant of the vehicle and an environment in which the vehicle is located, resulting in extracted features. The method can further include determining sentiment data representative of an emotional condition of the occupant of the vehicle based on an analysis of the extracted features, and generating a navigation route for the vehicle from an origin point to a destination point based on the sentiment data.

20 Claims, 11 Drawing Sheets

(51) Int. Cl.
    *G06V 20/59*         (2022.01)
    *G08B 21/06*         (2006.01)

(56)             References Cited

U.S. PATENT DOCUMENTS

| | | |
|---|---|---|
| 2014/0218187 A1 | 8/2014 | Chun et al. |
| 2015/0160019 A1 | 6/2015 | Biswal et al. |
| 2016/0104486 A1 | 4/2016 | Penilla et al. |
| 2017/0186315 A1 | 6/2017 | Glasgow et al. |
| 2017/0205240 A1 | 7/2017 | Nakamura et al. |
| 2017/0370732 A1 | 12/2017 | Bender et al. |
| 2017/0370744 A1 | 12/2017 | Miyajima |
| 2018/0061237 A1 | 3/2018 | Erickson et al. |
| 2018/0144746 A1 | 5/2018 | Mishra et al. |
| 2018/0164108 A1 | 6/2018 | Rahal-Arabi et al. |
| 2018/0172464 A1 | 6/2018 | Sekizawa et al. |
| 2019/0049261 A1 | 2/2019 | Colby |
| 2019/0220013 A1 | 7/2019 | Bradley et al. |
| 2019/0332902 A1 | 10/2019 | Gallagher et al. |
| 2020/0152197 A1 | 5/2020 | Penilla et al. |
| 2020/0309548 A1 | 10/2020 | Shintani et al. |
| 2020/0309549 A1 | 10/2020 | Aizawa et al. |

OTHER PUBLICATIONS

Kowalczuk, et al., "Emotion monitoring system for drivers", IFAC PapersOnline 52-8, 2019, 6 pages.

200

10

NAVIGATION DEVICE

FEATURE
EXTRACTION
COMPONENT

210

DATA FEATURES

CONDITION
REPRESENTATION
COMPONENT

220

SENTIMENT DATA

ROUTING
COMPONENT

230

NAVIGATION ROUTE

700

| | IN-VEHICLE SENSORS: MOTION, VIDEO, AUDIO, ETC. |
| | OUTSIDE VEHICLE SENSORS: MOTION, VIDEO, AUDIO, ETC. |
| | WEARABLE DEVICES: SMART WATCH, HEART MONITOR, ETC. |

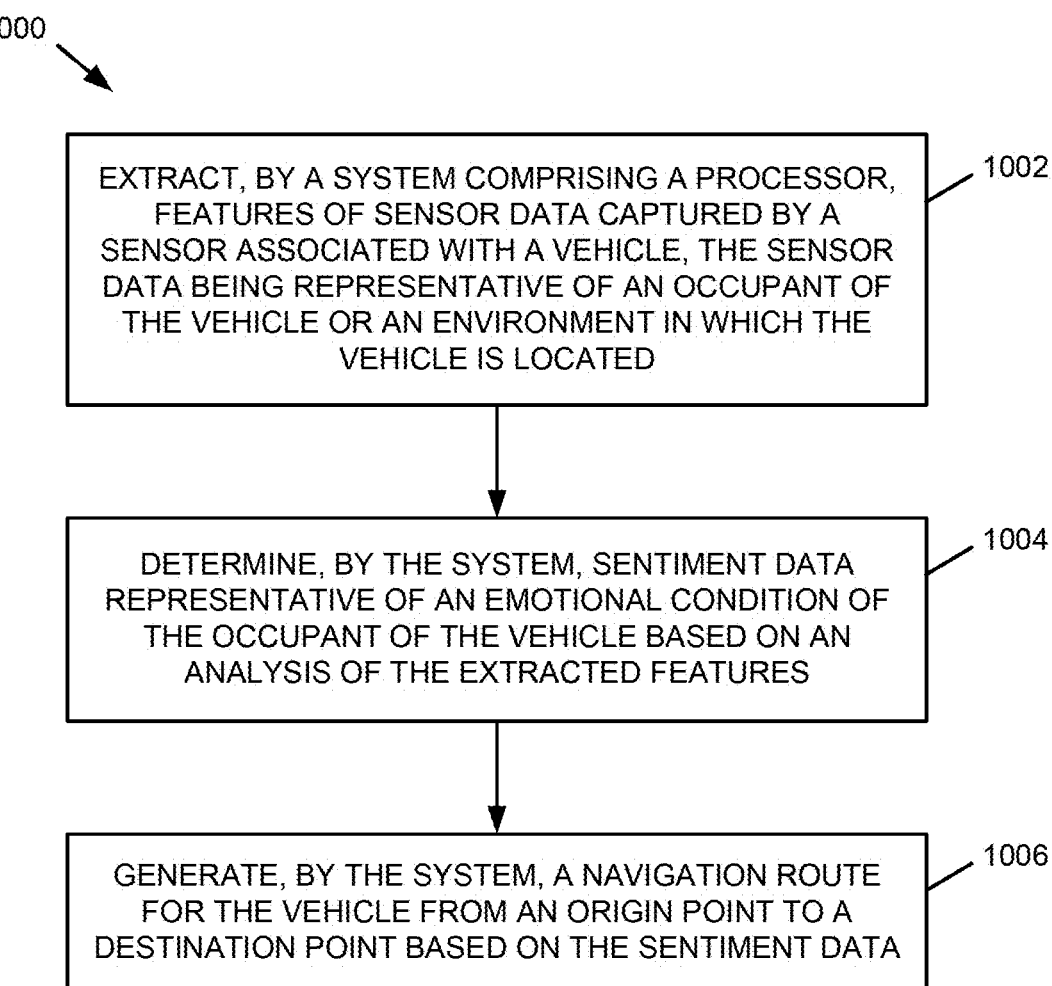

1000

EXTRACT, BY A SYSTEM COMPRISING A PROCESSOR, FEATURES OF SENSOR DATA CAPTURED BY A SENSOR ASSOCIATED WITH A VEHICLE, THE SENSOR DATA BEING REPRESENTATIVE OF AN OCCUPANT OF THE VEHICLE OR AN ENVIRONMENT IN WHICH THE VEHICLE IS LOCATED — 1002

DETERMINE, BY THE SYSTEM, SENTIMENT DATA REPRESENTATIVE OF AN EMOTIONAL CONDITION OF THE OCCUPANT OF THE VEHICLE BASED ON AN ANALYSIS OF THE EXTRACTED FEATURES — 1004

GENERATE, BY THE SYSTEM, A NAVIGATION ROUTE FOR THE VEHICLE FROM AN ORIGIN POINT TO A DESTINATION POINT BASED ON THE SENTIMENT DATA — 1006

FIG. 10

SENTIMENT-BASED NAVIGATION

CROSS-REFERENCE TO RELATED APPLICATION(S)

This application is a continuation of U.S. patent application Ser. No. 17/307,465 filed May 4, 2021. All sections of the aforementioned application(s) and/or patent(s) are incorporated herein by reference in their entirety.

TECHNICAL FIELD

The present disclosure relates to vehicle navigation systems, and, in particular, to techniques for creating or modifying vehicle navigation data.

BACKGROUND

Vehicle navigation applications, such as those employed by in-vehicle navigation systems, mobile device applications, or the like, can be utilized in combination with position location technologies such as the Global Positioning System (GPS) to guide a vehicle along a navigation route to a specified destination. Existing navigation systems can take into account the condition and characteristics of the vehicle (e.g., size and/or performance of the vehicle, remaining fuel, tire condition, etc.), as well as external factors such as traffic, road, and/or weather conditions along potential routes, in determining a navigation route to be followed. As vehicle technology advances, e.g., in the area of autonomous and/or semi-autonomous vehicles, vehicle navigation systems will become increasingly desirable in ensuring proper vehicle operation.

DESCRIPTION OF DRAWINGS

FIG. 10 is a flow diagram of a method that facilitates sentiment-based navigation in accordance with various aspects described herein.

DETAILED DESCRIPTION

Various specific details of the disclosed embodiments are provided in the description below. One skilled in the art will recognize, however, that the techniques described herein can in some cases be practiced without one or more of the specific details, or with other methods, components, materials, etc. In other instances, well-known structures, materials, or operations are not shown or described in detail to avoid obscuring certain aspects.

In an aspect, a method as described herein can include extracting, by a system including a processor, features of sensor data captured by a sensor associated with a vehicle, where the sensor data is representative of an occupant of the vehicle or an environment in which the vehicle is located, resulting in extracted features. The method can further include determining, by the system, sentiment data representative of an emotional condition of the occupant of the vehicle based on an analysis of the extracted features. The method can additionally include generating, by the system, a navigation route for the vehicle from an origin point to a destination point based on the sentiment data.

In another aspect, a system as described herein can include a processor and a memory that stores executable instructions that, when executed by the processor, facilitate performance of operations. The operations can include extracting features of data captured by a sensor associated with a vehicle, resulting in extracted data features, where the data captured by the sensor is representative of an occupant of the vehicle or an environment in which the vehicle is located; generating condition data representative of an emotional condition of the occupant of the vehicle by analyzing the extracted data features; and creating a navigation route for the vehicle from an origin point to a destination point based on the condition data.

In a further aspect, a non-transitory machine-readable medium as described herein can include executable instructions that, when executed by a processor, facilitate performance of operations. The operations can include determining data features that are representative of sensor data captured by a sensor associated with a vehicle, the sensor data including data representative of an occupant of the vehicle or an environment in which the vehicle is located; generating sentiment data representative of an emotional condition of the occupant of the vehicle according to the data features; and preparing route data representative of a navigation route for the vehicle from an origin point to a destination point based on the sentiment data.

Figure 1:
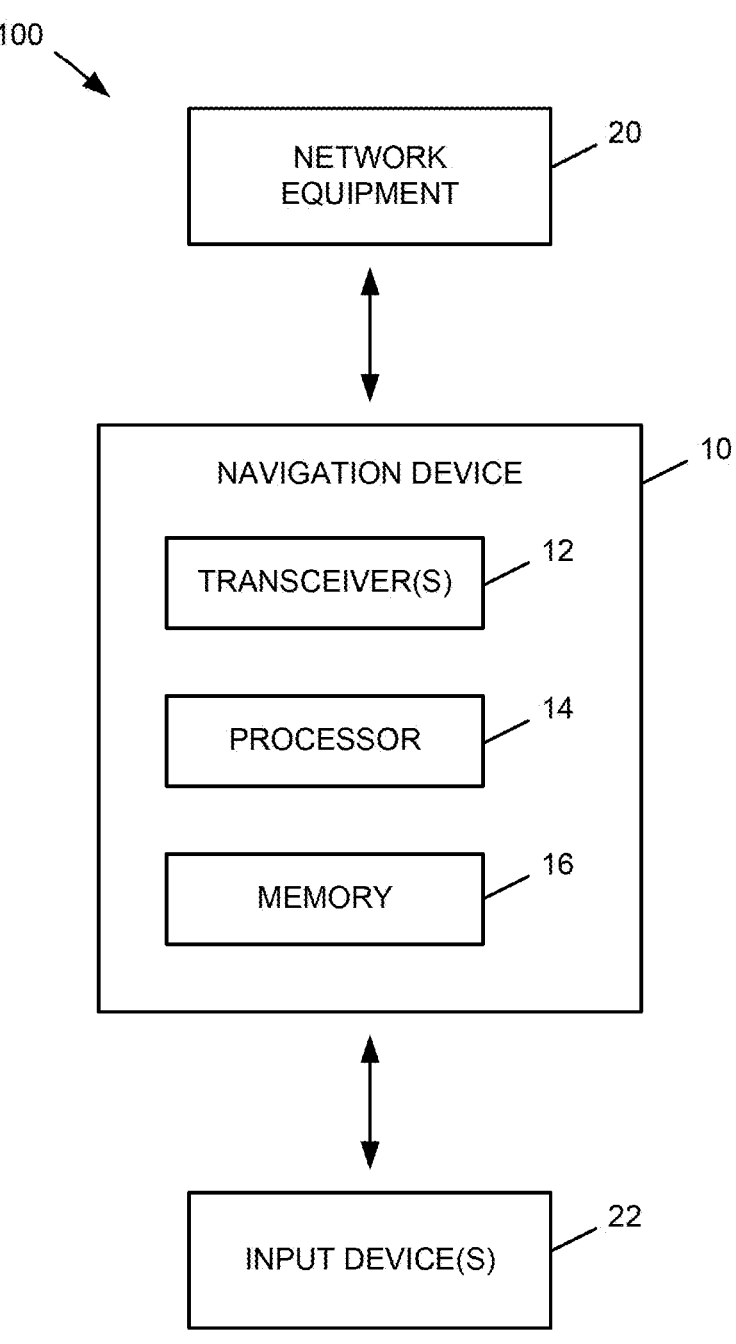
FIG. 1 is a block diagram of a system that facilitates sentiment-based navigation in accordance with various aspects described herein.

Referring first to FIG. 1, a system 100 that facilitates sentiment-based navigation is illustrated. System 100 as shown by FIG. 1 includes a navigation device 10 that can communicate with one or more other devices such as network equipment 20, one or more input devices 22, and/or other devices. In an aspect, the navigation device 10 can be utilized to facilitate navigation of a vehicle (e.g., an automobile, an airplane, etc.), either manually via a driver (pilot, captain, etc.) or automatically, e.g., in the case of an autonomous ("self-driving") or semi-autonomous vehicle. The navigation device 10 can be integrated into a vehicle, e.g., as an in-vehicle navigation system or the like, or alternatively the navigation device 10 can be implemented via an application executing on a mobile device such as a mobile phone, tablet or laptop computer, and/or any other suitable device that can provide navigation assistance to a vehicle and/or a driver of the vehicle. Other implementations are also possible.

The network equipment 20 shown in system 100 can include, and/or implement the functionality of, a network controller, a base station, an access point, an Evolved Node B (eNB), a next generation Node B (gNB), user equipment devices (UE) or other mobile devices, and/or any other devices that can communicate with the navigation device 10 over one or more communication networks. For instance, the network equipment 20 can include one or more remote servers that provide information to the navigation device 10 and/or assist the navigation device 10 in processing data, e.g., as will be described below with respect to FIG. 8.

The input devices 22 shown in system 100 can include various devices that provide input data to the navigation device according to various aspects as described below. For instance, input devices 22 can include one or more sensors (e.g., microphones or other audio sensors, cameras or other image/video sensors, motion sensors, temperature or pressure sensors, etc.) that provide sensor data input to the navigation device. In another example, input devices 22 can include mobile and/or wearable devices associated with occupants of the vehicle and/or other suitable devices that can provide relevant information to the navigation device 10. Examples of input devices that can be utilized by the navigation device are described in further detail below with respect to FIGS. 4-7.

In an aspect, the navigation device 10 can include one or more transceivers 12 that can communicate with (e.g., transmit messages to and/or receive messages from) the network equipment 20, the input devices 22, and/or other devices in system 100. The transceiver 12 can include respective antennas and/or any other hardware or software components (e.g., an encoder/decoder, modulator/demodulator, etc.) that can be utilized to process signals for transmission and/or reception by the navigation device 10 and/or associated network devices such as a base station.

In an aspect, the navigation device 10 can further include a processor 14 and a memory 16, which can be utilized to facilitate various functions of the navigation device 10. For instance, the memory 16 can include a non-transitory computer readable medium that contains computer executable instructions, and the processor 14 can execute instructions stored by the memory 16. For simplicity of explanation, various actions that can be performed via the processor 14 and the memory 16 of the navigation device 10 are shown and described below with respect to various logical components. In an aspect, the components described herein can be implemented in hardware, software, and/or a combination of hardware and software. For instance, a logical component as described herein can be implemented via instructions stored on the memory 16 and executed by the processor 14. Other implementations of various logical components could also be used, as will be described in further detail where applicable. In addition, an example computer architecture that can be utilized wholly or in part to implement various logical components described herein is described in further detail with respect to FIG. 11.

In an aspect, the processor 14 and the memory 16 of the navigation device 10 can provide enhanced navigation functionality by supplementing factors such as traffic, road, and weather conditions along a given route, vehicle properties, or the like, with additional data relating to the condition of occupants or users of a vehicle, such as a driver and/or passengers. For instance, the navigation device 10 can process information relating to the emotional condition, medical status, mood, behavior patterns, and/or other aspects of the condition of a driver or passengers of a vehicle in order to generate navigation routes that are tailored to the needs of individual occupants of the vehicle. In addition, the navigation device 10 as described herein can consider data such as driver experience, passenger preferences (e.g., occupants of a vehicle with a sleeping baby may prefer a smooth, quiet route, etc.), flexibility in arrival time, and/or other factors.

By implementing various embodiments as described herein, various advantages can be realized that can improve the performance of a vehicle and/or computing system that provides navigation functionality. These advantages can include, but are not limited to, the following. User satisfaction with respect to a navigation application can be improved by developing routes that better meet the needs of a specific driver and/or passenger. Vehicle safety can be improved by taking into consideration the medical and/or emotional status of the driver of a vehicle, as well as by ensuring that a selected navigation route will be appropriate for the skill level of the current driver. These safety improvements can also result in cost savings associated with fewer traffic accidents. Other advantages are also possible.

Figure 2:
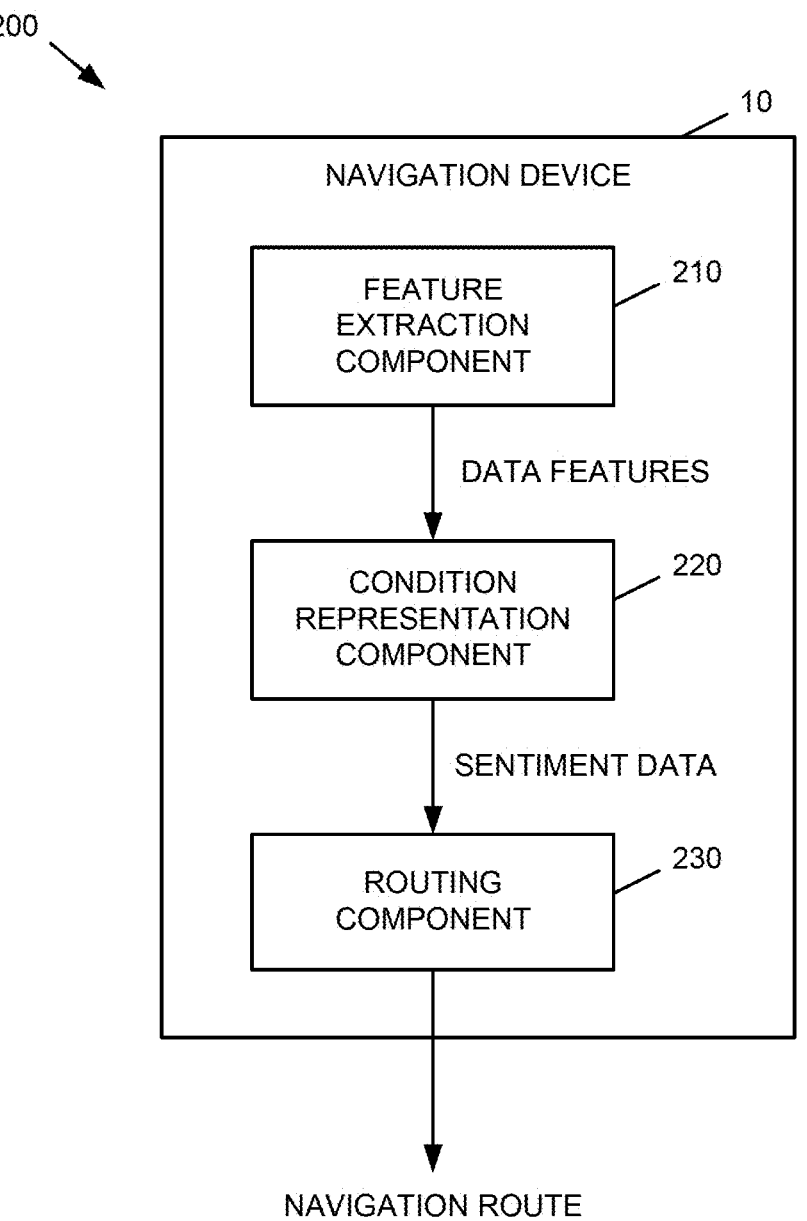
FIG. 2 is a block diagram that depicts the functionality of the navigation device of FIG. 1 in further detail in accordance with various aspects described herein.

With reference now to FIG. 2, a block diagram of a system 200 that facilitates sentiment-based navigation in accordance with various aspects described herein is illustrated. Repetitive description of like elements employed in other embodiments described herein is omitted for sake of brevity. System 200 as shown in FIG. 2 includes a navigation device 10 that can operate in a similar manner to that described above with respect to FIG. 1.

As shown in FIG. 2, the navigation device 10 of system 200 can include a feature extraction component 210 that can extract features from input data provided to the navigation device, e.g., features of sensor data captured by a sensor associated with the vehicle for which the navigation device 10 operates and/or other suitable data. In an aspect, the input data, and/or the features of the input data extracted by the feature extraction component 210, can be representative of a subject including, but not limited to, an occupant (driver or passenger) of the vehicle and/or an environment in which the vehicle is located. Example operation of the feature extraction component 210 is described in further detail below with respect to FIGS. 4-5, and example sensors that can provide data to be processed by the feature extraction component are described in further detail below with respect to FIG. 7.

The navigation device 10 of system 200 can further include a condition representation component 220 that can generate and/or otherwise determine sentiment data (also referred to herein as condition data) representative of an emotional condition of an occupant (driver, passenger, etc.) of the vehicle, e.g., based on an analysis of the features extracted by the feature extraction component 210. In addition to emotional condition, the sentiment data generated by the condition representation component 220 can also include data relating to a physical or medical state of the occupant, age and/or driving experience of the occupant, and/or other factors.

The navigation device 10 shown in system 200 can also include a routing component 230 that can generate a navigation route for the associated vehicle, e.g., from a specified origin point to a specified destination point, based on the sentiment data provided by the condition representation component 220. For example, based on a provided origin and destination, the routing component 230 can construct a navigation route connecting the origin and destination based, at least in part, on the sentiment data. Also or alternatively, the routing component 230 can modify an existing navigation route based on the sentiment data, e.g., to account for changes in driver and/or passenger condition over the course of the route.

Figure 3:
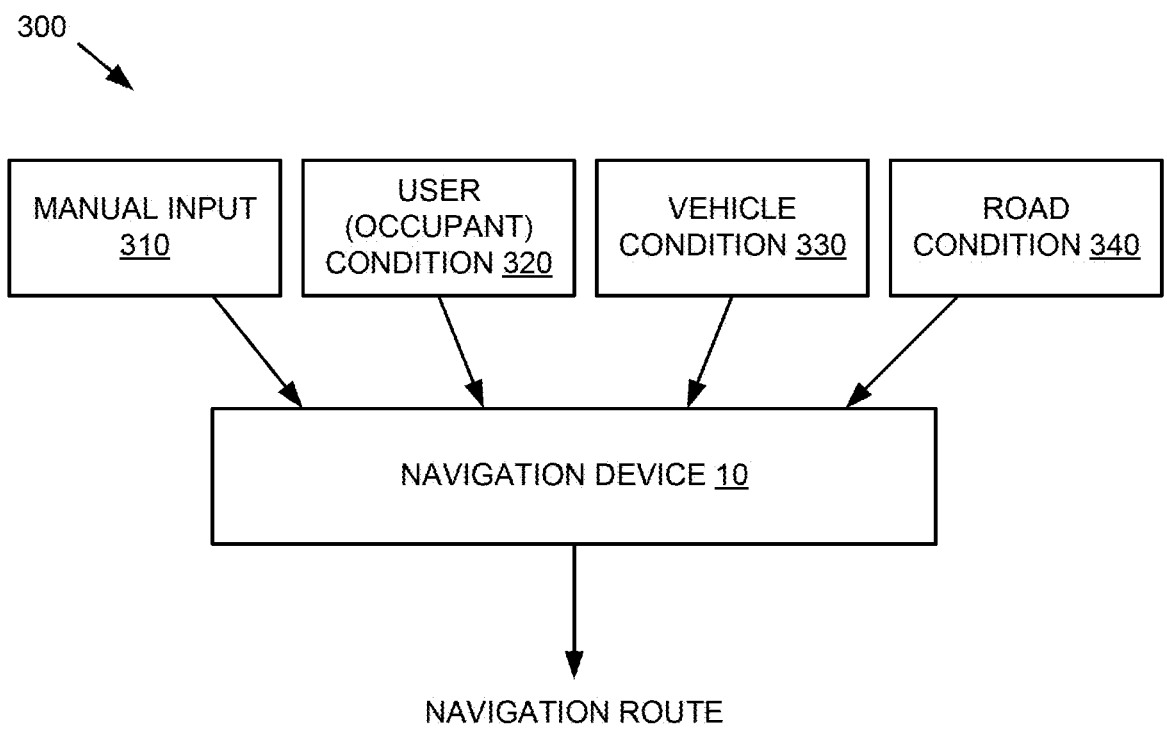
FIG. 3 is a diagram that depicts data types that can be utilized by the navigation device of FIG. 1 in accordance with various aspects described herein.

Turning now to FIG. 3, a diagram 300 is provided that depicts various types of data that can be utilized by the navigation device 10 as described above in accordance with various aspects described herein. It is noted that the types of data shown in diagram 300 are not intended to be an exhaustive listing of all data that can be considered by the navigation device 10, and that other types of data not shown in diagram 300 could be used in addition to, or in place of, the data types shown in diagram 300.

As shown in diagram 300, the navigation device 10 can receive manual input data 310, e.g., as provided via a user interface and/or other suitable means for accepting direct input from a user of the vehicle associated with the navigation device 10. The manual input data 310 can include, for example, preferences for a particular route, such as a preference for a more scenic route or a faster route, roadway preferences (e.g., prefer or avoid freeways, etc.), preferences regarding tolls, and/or similar factors. The manual input data 310 can also include an arrival time requirement (if any), e.g., if a user of the navigation device 10 is traveling to a doctor appointment and/or other time-sensitive event. Techniques that can be used by the navigation device 10 for manual input collection are described in further detail below with respect to FIG. 4.

User (or occupant) condition data 320, e.g., sentiment data as generated by the condition representation component 220 shown in FIG. 2, can include information relating to the condition of one or more users of the associated vehicle, such as a driver of the vehicle and/or one or more passengers. It is noted that in the case of an autonomous or semi-autonomous vehicle, each occupant of the vehicle can be regarded by the navigation device 10 as a passenger under typical conditions, e.g., such that the vehicle has no human driver in said circumstances.

In an aspect, the user condition data 320 shown in diagram 300 can include data relating to the physical state of one or more users of the vehicle. Physical state data can include, for example, data indicative of a level of fatigue and/or alertness of a driver or other user of the vehicle. This data can take the form of a simple indication that a driver or other user of the vehicle appears to be tired, or alternatively more granular data can be collected and/or used. Physical state data can also include data relating to the personality of a vehicle user, e.g., whether the user is easily excitable or distracted. Physical state data can additionally include data regarding the health status of a vehicle user, e.g., in order to determine whether a driver or other vehicle user is feeling unwell due to illness or other causes.

In another aspect, the user condition data 320 can include information pertaining to the emotional state of one or more users of the vehicle. Emotional state data can be used, for example, to determine whether a driver or other vehicle user experiences anxiety from driving situations such as high speed highways, narrow roadways or alleys, bridges or other elevated roadways, driving at night and/or in low-visibility conditions, and/or other circumstances. Emotional state data that can be utilized by the navigation device 10 in this manner can include indicators of stress or distraction present in a user's voice, user heart rate or other medical statistics, frequency of head and/or eye movement in scanning the upcoming roadway (e.g., more rapid head or eye movements can in some cases be an indicator of stress), an amount of pressure applied by a user to a steering wheel or other control mechanisms of the vehicle (e.g., higher pressure exerted by the user can in some cases indicate a heightened degree of stress), and/or other suitable data.

The user condition data 320 can additionally include information relating to a level of distraction associated with a driver or other user of the vehicle. For example, data indicating that a user is engaged in a highly interactive conversation on the telephone and/or with other users of the vehicle can be used by the navigation device 10 in making an inference that the driver or other user(s) of the vehicle is potentially distracted. Similarly, data indicating that a vehicle user is fidgeting or changing vehicle settings (e.g., seat positioning, selecting music, radio stations, or other media to be played in the vehicle, etc.) can also be used to infer a higher level of distraction. In another example, a level of distraction can be determined based on sounds and/or other events that are external to the vehicle, such as sirens, nearby traffic accidents, or the like.

In a further aspect, the user condition data 320 shown in diagram 300 can additionally relate to the level of driving experience associated with a driver of the vehicle, or in the case of an autonomous vehicle, a user of the vehicle that is expected to assume control of the vehicle if autonomous control of the vehicle fails or is disabled. For example, the navigation device 10 can prioritize less congested and/or better marked routes in the case of an inexperienced driver, e.g., as opposed to more difficult routes that may be faster than the prioritized route.

In still another aspect, the user condition data 320 can include data representative of the preferences of one or more passengers of the vehicle. For instance, if the user condition data 320 indicates that a sleeping baby is present in the vehicle, the navigation device 10 can be configured to avoid noisy routes, routes with high numbers of intersections and/or changes in speed, or the like. In another example, if the user condition data 320 indicates that an elderly person is driving or present in the vehicle, the navigation device 10 can prioritize routes that include smoother and well-lit roads over other alternatives. A preference for roadway lighting made in this manner can also depend on the time of day, e.g., such that roadway lighting is given a higher priority at night than during the day when natural lighting may be sufficient.

The user condition data 320 can also include data representative of the importance of arriving at a given destination at a specific time. For instance, the navigation device 10 may prioritize faster routes in cases where a user must arrive at a given destination by a specific time (e.g., for a doctor's appointment or the like) while prioritizing more scenic or easier routes when the arrival time is more flexible.

Vehicle condition data 330 as shown by diagram 300 can include respective properties of the vehicle associated with the navigation device 10 that could affect the ability of the vehicle to complete a given navigation route. Vehicle condition data 330 as shown in diagram 300 can include, but is not limited to, the following:

1) Vehicle shape and/or dimensions, e.g., to enable the navigation device 10 to avoid generating routes on narrow streets if the vehicle is overwide for said streets.
2) Vehicle speed, e.g., such that the navigation device 10 can determine whether the vehicle can match the current minimum speed assigned to respective roadways.
3) Maintenance history, such as last maintenance time or the like. In an aspect, the navigation device can use maintenance history data to estimate the likelihood of a vehicle breakdown, which can in turn be used by the navigation device 10 in route selection. For instance, if the navigation device 10 determines that a vehicle is likely to encounter a breakdown, the navigation device 10 can avoid setting navigation routes in remote areas and/or areas without adequate service stations.

4) Fuel level, e.g., such that the navigation device 10 can select a route with more gas stations if the fuel level is determined to be low, or with less or no gas stations if the navigation device 10 determines that refueling is not likely to be needed along the route. In an implementation in which the navigation device 10 is associated with an electric vehicle, the navigation device 10 can perform similar actions with regard to vehicle battery charge level and availability of charging stations.

5) Engine condition, e.g., which can be used by the navigation device 10 to select routes that are appropriate for a given vehicle's engine capability.

6) Other vehicle capabilities, such as drivetrain (all-wheel or front-wheel drive, etc.), tire condition, etc.

As further shown in diagram 300, road condition data 340 can include data representative of the conditions of respective candidate roadways for a navigation route. Road condition data 340 can include, but is not limited to, weather conditions (e.g., whether the road is wet or covered in snow or ice), speed limit, placement of and/or distance between intersections, and/or other information. Road condition data 340 as shown in diagram 300 can also include information relating to lighting conditions for respective roadways, e.g., which can be considered in selecting a navigation route for a given driver based on their user condition data 320 as described above. In another example, road condition data 340 can include information relating to presence and/or visibility of line markings on a given roadway, which can be considered by the navigation device 10, e.g., in determining a navigation route for an autonomous vehicle that utilizes line markings for directional guidance.

In addition to the types of information shown in diagram 300, the navigation device 10 could also receive and utilize other types of data. For instance, if the navigation device 10 is operating in an area with high speed, low latency network communications, the navigation device 10 could further leverage information from one or more remote sources, such as image processing data from a satellite system that indicates upcoming driving conditions on a given roadway, e.g., in terms of obstructions, weather, or other road conditions, traffic conditions, or the like). Additionally, in a scenario in which multiple vehicles are traveling in close proximity, a navigation device 10 at a given vehicle could leverage vehicle platooning in order to share data with other nearby vehicles and/or other data sources. As another example, the navigation device 10 could obtain information and/or route recommendation data from one or more remote servers, as will be discussed in further detail below with respect to FIGS. 8-9.

Figure 4:
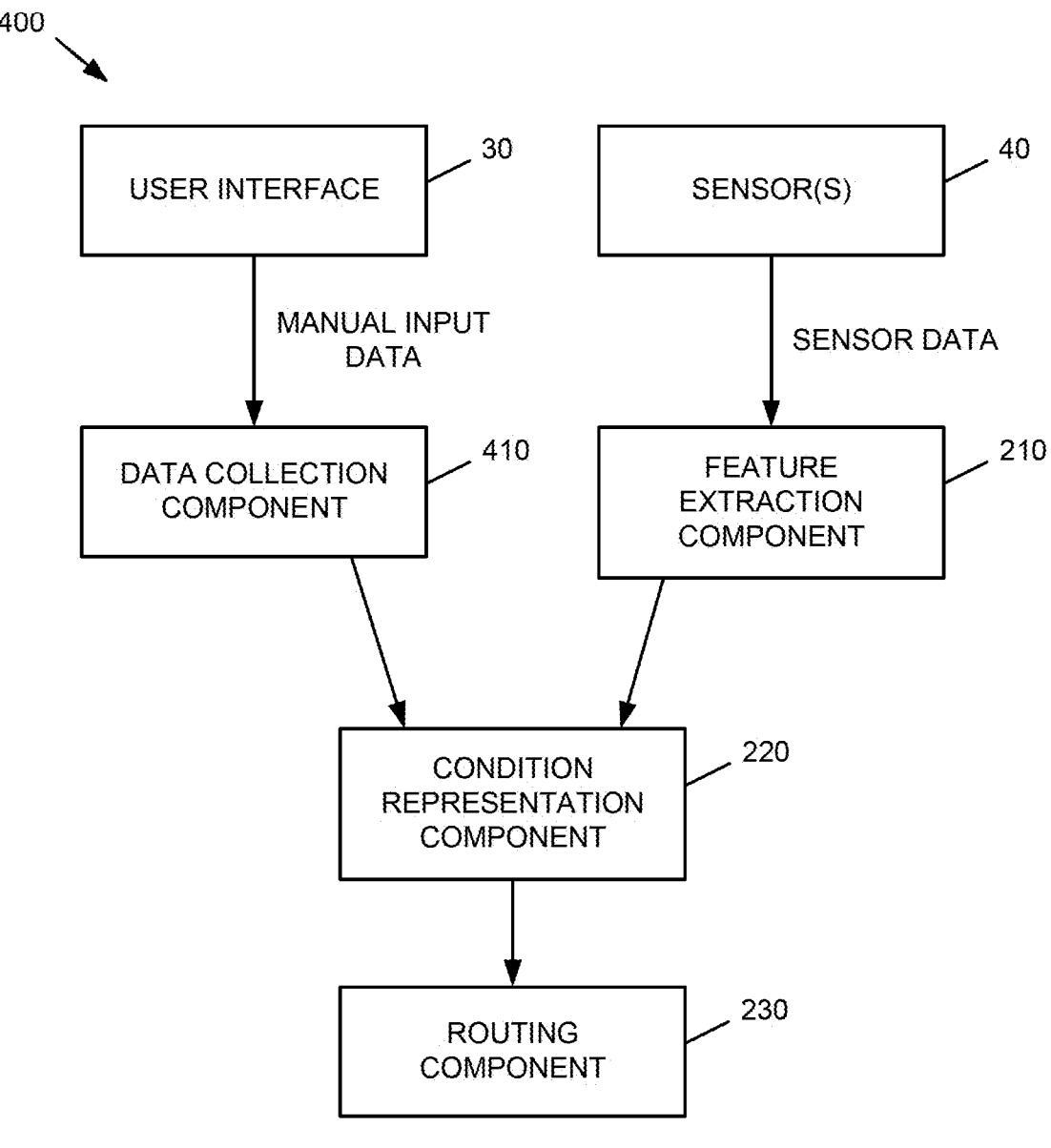
FIG. 4 is a block diagram of a system that facilitates data collection for a vehicle navigation system in accordance with various aspects described herein.

Referring next to FIG. 4, a block diagram of a system 400 that facilitates data collection for a vehicle navigation system in accordance with various aspects described herein is illustrated. Repetitive description of like elements employed in other embodiments described herein is omitted for brevity. As shown in FIG. 4, system 400 includes a user interface 30, which can include one or more input devices (e.g., touch screen, microphone, keypad, etc.) through which a user of a vehicle can provide manual input, e.g., manual input data 310, to system 400. Additionally, the user interface 30 can include one or more output devices, such as a display (a display screen, a hologram, a windshield heads-up display HUD), etc.), speakers, or similar devices for conveying information to the user. Also or alternatively, the user interface 30 can be implemented via an application on a mobile device associated with a user, such as a smartphone navigation application or other similar applications.

In an aspect, input data can be received from the user interface 30 via a data collection component 410, which can provide the input data to the condition representation component 220 for generation of sentiment data, e.g., as described above with respect to FIG. 2. As additionally shown in FIG. 4, collection of manual input data via the data collection component 410 can occur together with collection of data from one or more sensors 40 (e.g., audio sensors, video sensors, motion sensors, etc.) via the feature extraction component 210 as described above.

In an aspect, the user interface 30 can enable a user to input requests or needs associated with a given navigation route. For instance, a user can provide the origin point and destination for a given route to system 400 via the user interface. Alternatively, one or more of the origin point or destination for a given route could be assumed or automatically entered in the user interface 30 based on data pertaining to the user such as the user's home or work address, the user's calendar data (e.g., to auto-fill the address of a doctor's office for an upcoming doctor's appointment, etc.), and/or other data. In some implementations, data pertaining to a given user can be collected from one or more devices associated with that user, e.g., as described below with regard to FIG. 6. In the event that automatically entered data is inaccurate for a given route, the user can modify the inaccurate information via the user interface 30.

In another aspect, a user can provide one or more requests for a given route via the user interface 30. For instance, a user can specify a preference for a more scenic route (e.g., as opposed to a faster but less scenic route) as well as preferences for toll roads, route speed versus distance (e.g., whether a user prefers the fastest route or the shortest route), etc. Additionally, a user can specify the relative importance of an on-time arrival via the user interface 30, which can be utilized by the routing component 230, e.g., to restrict candidate routes to only those routes that would reach the route destination by at least a given amount of time before the designated arrival time if an on-time arrival is specified as highly important.

A user can also provide, via the user interface 30, information regarding one or more passengers of the vehicle, which can be further used by the routing component 230 in generating a navigation route. For example, if a user specifies via the user interface 30 that a sleeping baby is in the car, the routing component 230 can prioritize smoother and quieter roads over alternatives. Additionally, some user preference information could be assumed or automatically entered based on other contextual data. For instance, if a user's calendar indicates that the user is on vacation, the user interface 30 can mark a more scenic route as a default route even if the user has specified a preference for faster routes in the past.

In an aspect, system 400 can prioritize safety and needs over specific requests provided via the user interface 30. For instance, the routing component 230 can generate a navigation route that differs from the preferences specified by a user via the user interface 30 if system 400 determines that the vehicle is not capable of reliably completing a requested route, e.g., due to inadequate vehicle condition. Additionally, the routing component 230 can select a route that includes a fuel or charging station in response to determining that the vehicle's fuel or charge level is not sufficient to complete the route, e.g., even if the user does not indicate a preference for a fuel or charging station.

In another aspect, the user interface 30 can be utilized by multiple users of a vehicle to indicate individualized user preferences for a given route, and the routing component 230 can synthesize the received preferences from all users to generate a route that best accommodates all user requests. In the event that no priority manual input is specified (e.g., a driver's preferences can be prioritized over passenger preferences, a given user's preferences can be manually assigned higher priority, etc.), the routing component 230 can prioritize the needs or requests of the most vulnerable vehicle user, e.g., a sleeping baby, an elderly person, a person determined by the condition representation component 220 to be physically ill or stressed, etc.

The user interface 30 shown in system 400 can further be used to facilitate communication between system 400 and respective users of a vehicle. In an implementation in which a navigation device 10 is integrated into a vehicle control system, the vehicle control system can implement some or all of the functionality of the user interface in order to communicate with the vehicle users, e.g., via an in-vehicle hologram, a HUD, and/or other suitable interface types. By way of example, a vehicle can, e.g., via a hologram, ask a user whether a generated navigation route is satisfactory. The user can respond to this inquiry by speaking back to the hologram and/or performing any other action(s) suitable to convey feedback via the user interface 30.

In addition, a vehicle, through the user interface 30, can provide aid or suggestions to a user in response to the sentiment data for that user indicating a need for such assistance. For example, if a user is showing signs of stress, the user interface 30 can take actions such as playing the user's favorite song, providing affirmations, etc. Similarly, if a driver appears tired, the user interface 30 can direct the user to a motel or service area, recommend a break, etc. In another example, if a user indicates via the user interface 30 that the user is experiencing motion sickness, the routing component 230 can modify a navigation route to alleviate the motion sickness, e.g., by selecting a new route with less turns or elevation changes. Other, similar actions could also be performed.

Figure 5:
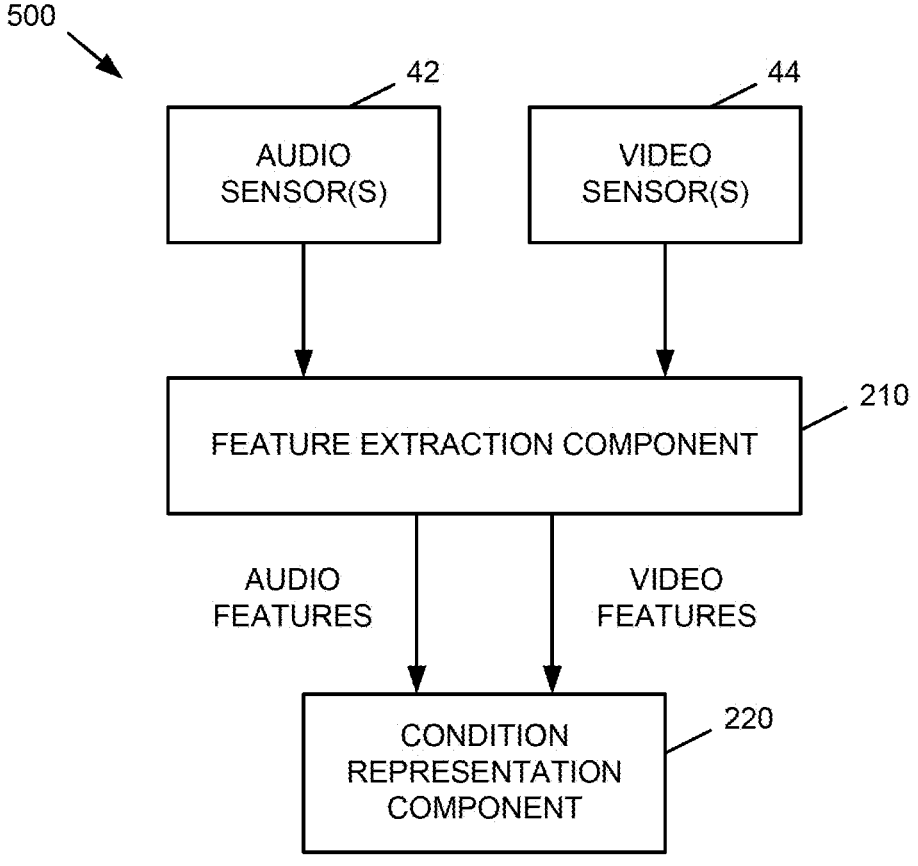
FIG. 5 is a block diagram of a system that facilitates extraction of sensor data features for sentiment-based navigation in accordance with various aspects described herein.

As noted above, manual input data provided via the user interface 30 can be utilized in combination with sensor data features, e.g., features of sensor data that are extracted from the feature extraction component 210 based on data collected by one or more sensors 40. With reference now to FIG. 5, a system 500 that facilitates extraction of sensor data features for sentiment-based navigation in accordance with various aspects described herein is illustrated. Repetitive description of like elements employed in other embodiments described herein is omitted for sake of brevity. As shown in FIG. 5, the feature extraction component 210 of system 500 can receive as input data from respective sensors, such as audio data captured by an audio sensor 42 and/or video data captured by a video sensor 44. The feature extraction component 210 can then output extracted features, e.g., audio features and video features in the example shown by system 500, to the condition representation component 220 for computation of sentiment data. While system 500 as shown in FIG. 5 includes only an audio sensor 42 and a video sensor 44, it is noted that other types of sensors, such as a motion or movement sensor, a temperature sensor, etc., could also be used in addition to, or in place of, the audio sensor 42 and video sensor 44.

In the description that follows, respective example use cases for input data received via respective sensors, e.g., an audio sensor 42 and/or a video sensor 44, are provided. It is noted that the following examples are not intended to be an exhaustive listing of inputs that can be processed by the feature extraction component 210 and that other examples are also possible.

In an aspect, audio data received by the feature extraction component 210, e.g., from the audio sensor 42, can include data that is representative of speech uttered by (originating from) a user or occupant of a vehicle, e.g., during a conversation between passengers, a telephone conversation, and/or other scenarios. Based on this input, the feature extraction component 210 can extract properties of the speech that can include voice tones present in the speech, content of the speech, or the like. By way of example, the feature extraction component 210 can extract the tone of a user's speech to detect stress, aggression, frustration, boredom, whether the driver is in a hurry, etc. As another example, the feature extraction component 210 can perform speech to text processing in order to detect respective keywords that could give cues as to the user's sentiment. As a further example, the feature extraction component 210 can detect properties of specific speech inputs, e.g., the amount of happiness or sadness in a user's voice when saying a destination address for a navigation route, etc.

In another aspect, the feature extraction component 210 can detect audio events in or around an associated vehicle (e.g., a horn honking, a siren, a telephone ringing inside the vehicle, etc.). In response, the feature extraction component 210 can classify the audio event and provide this classification to the condition representation component 220 to aid in determining corresponding sentiment data. By way of example, the feature extraction component 210 can compare an amount of audio activity present in audio data captured by the audio sensor 42 to a defined baseline amount of audio activity, which can be a global baseline or a baseline specific to a given vehicle and/or user. If the amount of audio activity is greater than the baseline, the feature extraction component 210 can identify the increased activity as an audio event to be processed as described above. Additionally, the feature extraction component 210 can estimate a level of distraction associated with the present amount of audio activity. For instance, in response to detecting a high level of audio activity, or audio activity of specific types (e.g., sirens, a crying baby, etc.), the feature extraction component 210 can infer that the potential for distraction is higher relative to a baseline. This information can then be provided to the condition representation component 220 to be used in determining sentiment data corresponding to the potential for distraction.

In a further aspect, video data received by the feature extraction component, e.g., from the video sensor 44, can include a depiction of an occupant (driver or passenger) of the associated vehicle. From this data, the feature extraction component 210 can extract or otherwise identify properties present in the video data such as movement and/or posture of the vehicle occupant. These extracted properties can then be provided to the condition representation component 220 for determination of appropriate sentiment data.

By way of example, the feature extraction component 210 can detect features from video data depicting a vehicle occupant that is representative of the condition of that occupant. For instance, video data depicting a vehicle occupant fidgeting with vehicle controls and/or an object such as a pen can contribute to a determination that the occupant is stressed. The feature extraction component 210 can further analyze movement of an occupant's head, arms, or legs, as well as the occupant's posture, to determine whether the occupant is drowsy, agitated, etc. For instance, a driver of a vehicle could be classified as drowsy if the video data indicates that the driver's head is slumping forward, the driver is blinking at a reduced rate, etc. Events occurring outside the vehicle, such as a passenger slamming a door or the trunk of the vehicle, a driver or passenger being hesitant to enter the vehicle or close the vehicle doors, etc., could also be considered in determining sentiment data. As a further example, the spacing between passengers as depicted in video data could further be used to determine attitudes or familiarity between passengers, e.g., such that passengers spaced further apart could be regarded as less intimate as passengers spaced closer together.

Additionally, the feature extraction component 210 could supplement video data provided via a video sensor 44, and/or other data types, with motion and/or movement input captured by a motion sensor, accelerometer, or similar sensor associated with the vehicle. In an aspect, the feature extraction component 210 can capture context and/or further information that is not captured by other sensors such as video, e.g., subtle movements in a driver's seat that can be detected by movement sensors but not video. Additionally, motion or movement sensors can be used to monitor movement of passengers and/or pets in the vehicle, which could be determined to be a distraction in some cases.

In an aspect, data features captured by the feature extraction component 210 and provided to the condition representation component 220 can be used either to generate a navigation route or to modify an existing navigation route. For instance, if a navigation route is initially determined based on sentiment data for a user computed via initial sensor data, changes to the sentiment data of the user as detected by the feature extraction component 210 during traversal of the route can be used to modify the navigation route as appropriate.

Figure 6:
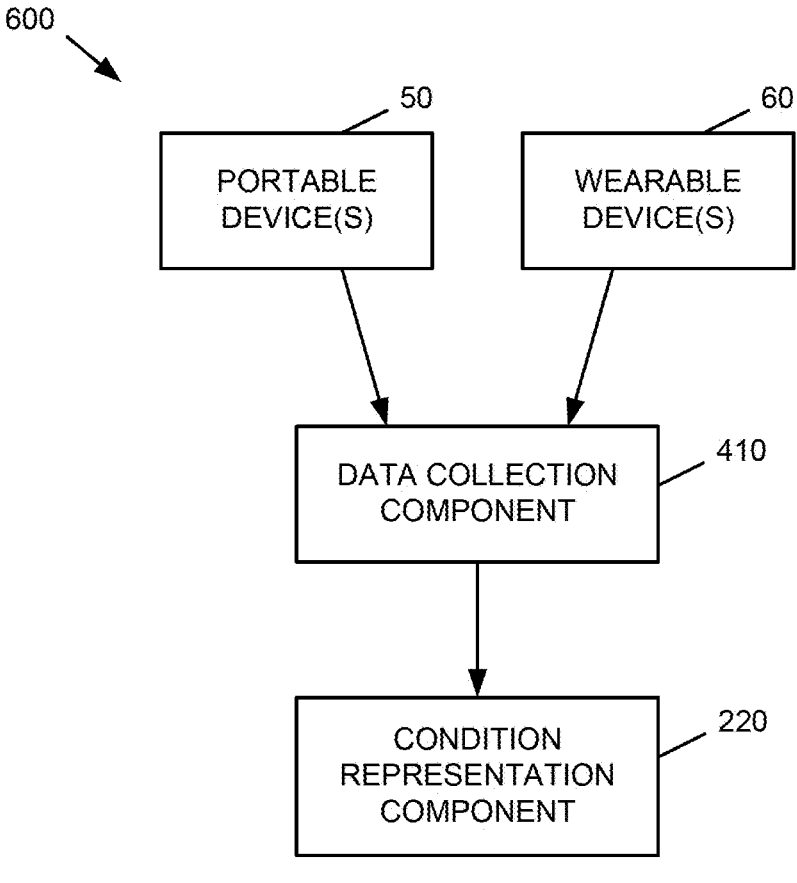
FIG. 6 is a block diagram of a system that facilitates integration of user devices with a vehicle navigation system in accordance with various aspects described herein.

Turning now to FIG. 6, a block diagram of a system 600 that facilitates integration of user devices with a vehicle navigation system in accordance with various aspects described herein is illustrated. Repetitive description of like elements employed in other embodiments described herein is omitted for sake of brevity. As shown in FIG. 6, a data collection component 410 of system 600 can obtain device data from one or more devices associated with a user of an associated vehicle, such as portable (mobile) device 50 and/or wearable devices 60. In an aspect, the data collection component 410 can collect data from devices 50, 60 pursuant to a data collection agreement executed by the user and/or other techniques by which affirmative consent for data collection can be provided by the user. Device data collected by the data collection component 410 in this manner can then be provided to the condition representation component 220 to determine sentiment data corresponding to the device data.

In an aspect, the portable devices 50 shown in system 600 can include one or more mobile or portable computing devices associated with a given user, such as a mobile phone, a laptop or tablet computer, or the like. Device data collected from the portable devices 50 by the data collection component 410 can include, but is not limited to, appointments or calendar data associated with the user, user chat or text messages, contacts, personal information such as home address and/or phone number, etc.

The wearable devices 60 shown in system 600 can include wearable computing devices such as smart watches, medical devices such as pacemakers or insulin pumps, and/or any other suitable devices. In an aspect, the data collection component 410 can collect medical data, such as heart rate or the like, and or other suitable data from respective wearable devices 60.

In addition to the data described above, the data collection component 410 could also utilize other information provided by the user (e.g., via the user interface 30 shown in FIG. 4), such as data relating to a medical history or medical conditions associated with the user and/or any other information that can be provided by a user that would be desirable in determining sentiment data.

Figure 7:
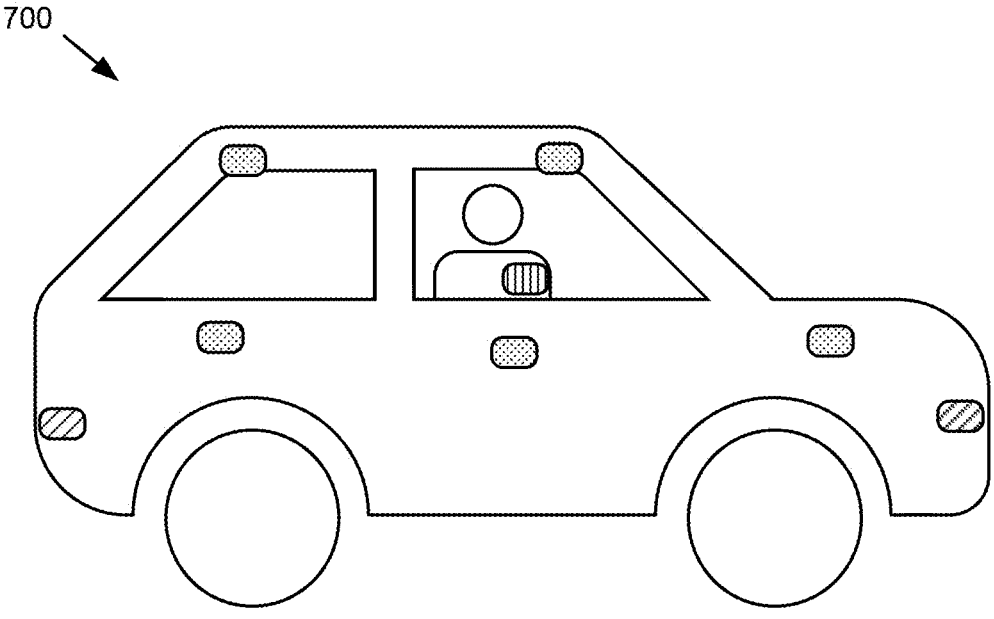
FIG. 7 is a diagram that depicts data sources that can be utilized by a vehicle navigation system for sentiment-based navigation in accordance with various aspects described herein.

With reference now to FIG. 7, diagram 700 depicts data sources that can be utilized by a vehicle navigation system (e.g., implemented by a navigation device 10) for sentiment-based navigation in accordance with various aspects described herein. The data sources shown in diagram 700 include one or more sensors 40 (e.g., audio sensors 42, video sensors 44, motion sensors, etc.), which can be placed both inside and outside of the vehicle. In this manner, data collection by the respective sensors 40 can be focused based on the location of a given sensor 40 with respect to the vehicle. For instance, in-vehicle sensors can capture data relating to occupants of the vehicle, e.g., as described above, while the external sensors can capture data relating to events occurring outside of the vehicle such as approaching vehicles, pedestrians and/or animals entering the roadway, or the like. As further shown in diagram 700, data captured by one or more wearable devices 60 associated with a vehicle occupant can also be utilized.

Figure 8:
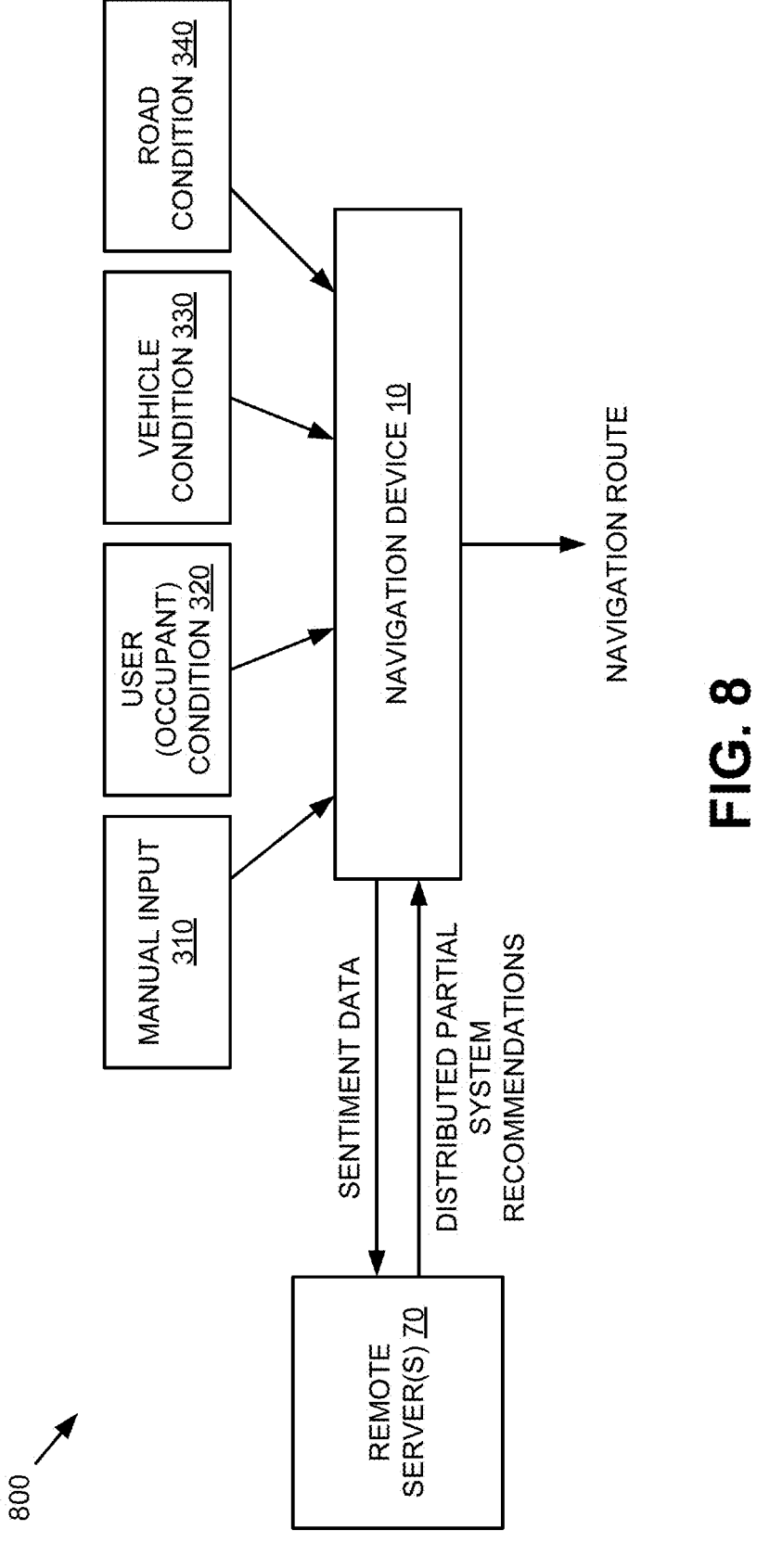
FIG. 8 is a block diagram of a system that facilitates distributed route processing in a vehicle navigation system in accordance with various aspects described herein.

Referring now to FIG. 8, a block diagram of a system 800 that facilitates distributed route processing in a vehicle navigation system in accordance with various aspects described herein is illustrated. Repetitive description of like elements employed in other embodiments described herein is omitted for sake of brevity. As shown in FIG. 8, the navigation device 10 of system 800 can collect respective types of data, such as manual input data 310, user (occupant) condition data 320, vehicle condition data 330, and road condition data 340, in a similar manner to that described above with respect to FIG. 3. In addition, system 800 includes a remote server 70 that can assist the navigation device 10 by providing distributed processing and/or data collection functionality. For instance, as shown in FIG. 8, the navigation device 10 of system 800 can transmit generated sentiment data (e.g., sentiment data generated by a condition representation component 220) to the remote server. In response, the navigation device 10 can receive route recommendation data, e.g., in the form of distributed partial system recommendations, from the remote server 70. The navigation device 10 can then utilize this route recommendation data, in addition to or in place of locally generated data, in determining a navigation route for an associated vehicle.

In an aspect, the remote server 70 shown in system 800 can be a Sentiment Repository and Predictive Server (SRP), which can reside in the core or edge of the navigation service provider associated with the navigation device 10. The SRP can be, for example, a machine learning powered system that collects information about users, such as their mood and their travel preferences. The SRP can additionally or alternatively collect data pertaining to demographics associated with a user, user location, profession, time of day and/or season, music preferences, and/or any other suitable data. These and/or other data collected by the SRP can be gathered and/or learned over time.

In another aspect, in-vehicle sensors (e.g., as depicted in diagram 700) can collect passenger information and their sentiment. Subsequently, the navigation device 10 can query the SRP regarding suggestions for improving the personal sentiment of the passengers during the ride. These suggestions can include, but are not limited to, playing a particular song, movie, or other media, recommending speed changes, etc.

The navigation device 10 and/or SRP (or other remote server 70) can further determine routing information based on respective baselines. In an aspect, system 800 can use two levels of baselining: a global baseline relative to generic behavior of the population that is stored at the SRP, and a local baseline that pertains to the specific users of a given vehicle as stored by the local navigation device 10. In the event that these baselines conflict, the navigation device 10 can prioritize more specific baseline data over a generic baseline.

In an aspect, an input signal, such as audio, can be initially processed by the local navigation device 10 to detect behaviors or other features of the data. The navigation device 10 can then query the SRP for additional guidance as desired, e.g., if the navigation device 10 detects new passengers or behaviors and/or other events for which local knowledge is not present. In response, the SRP can provide output representative of a best route for the vehicle, e.g., based on past experiences (both local to the navigation device 10 and global) that made similar rides more enjoyable.

Figure 9:
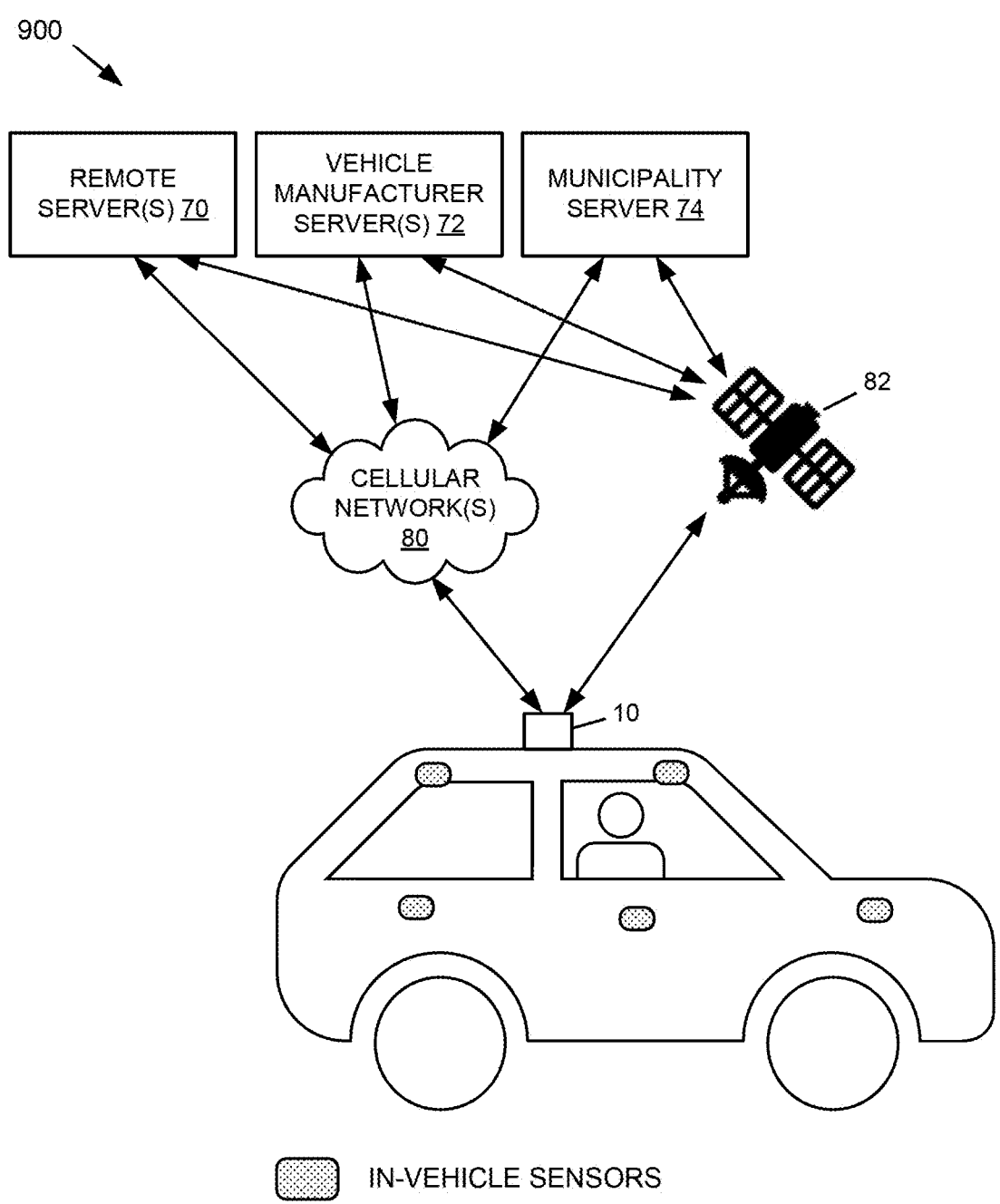
FIG. 9 is a diagram that depicts an example network environment in which various embodiments described herein can function.

Turning next to FIG. 9, a diagram that depicts an example network environment in which various embodiments described herein can function is illustrated. Repetitive description of like elements employed in other embodiments described herein is omitted for sake of brevity. In an aspect, system 900 can facilitate a distributed decision making process for navigation of a vehicle associated with a navigation device 10. While the navigation device 10 is illustrated in FIG. 9 as external to the vehicle for purposes of visual clarity, it is noted that that navigation device 10 could be positioned in any suitable manner for providing navigation functionality to its associated vehicle.

As shown in FIG. 9, the navigation device 10 of system 900 can collect data from one or more in-vehicle sensors, e.g., in a similar manner to that described above with respect to FIG. 7. While not shown in FIG. 9, the navigation device 10 could also leverage additional sensors, such as external sensors, wearable devices, or the like, as further described above with respect to FIG. 7. As further shown in FIG. 9, the navigation device 10 can access information and/or recommendation data from external sources, such as a remote server 70 (e.g., an SRP, etc.), a vehicle manufacturer server 72 for the vehicle associated with the navigation device 10, a municipality server 74 associated with a current location of the vehicle, and/or other sources.

The navigation device 10 and the servers 70, 72, 74 can communicate with each other via one or more cellular networks 80, such as a fifth generation (5G) or sixth generation (6G) network. Also or alternatively, the navigation device 10 can communicate with the servers 70, 72, 74 via a satellite communication system 82 and/or one or more other networks that provide broader communication coverage for the vehicle, e.g., if sufficient cellular service is not available at the location of the vehicle. In addition to the servers 70, 72, 74 shown in system 900, the navigation device 10 can also communicate with other devices such as edge devices along its navigation route, navigation devices 10 associated with other vehicles, mobile devices in the area of the vehicle, and/or other devices to facilitate calculations for expedited data processing and load distribution.

As a specific, non-limiting example of communications that can be conducted in system 900 for an electric vehicle traveling along a highway, an edge node associated with a cellular network 80 located a few miles down the highway can anticipate that the vehicle will pass by it, e.g., via vehicle-to-vehicle or vehicle-to-infrastructure communication, GPS tracking, etc.). In response, the edge node can obtain vehicle data from the vehicle itself (e.g., battery charge level, etc.), as well as data from the vehicle manufacturer server 72 pertaining to the make and model of the vehicle, in order to determine whether the vehicle should continue on its current route. The edge node can then transmit this partial decision to the navigation device 10 associated with the vehicle to be considered in the overall decision process. In some cases, the navigation device 10 could also obtain partial decision data from navigation devices 10 associated with other vehicles. For instance, satellite image data for an area can be distributed among multiple navigation devices 10 for processing to case the processing burden on any single navigation device 10 in the area.

In an aspect, a navigation device 10 can leverage a distributed system, such as system 900, to determine and process vehicle condition data 330, e.g., as shown by FIG. 8, as follows. Initially, the navigation device 10 can connect to the engine and respective sensors of the vehicle to obtain information such as battery or fuel level, oil condition, brake condition, etc. Additionally, the navigation device can obtain information from the vehicle such as its unloaded or loaded weight, its width, current tire depth and/or tire characteristics, and/or other information. The navigation device 10 can additionally connect to the vehicle manufacturer server 72 for recommendations regarding safe operating conditions for the vehicle, e.g., with respect to tire levels, battery life, vehicle condition, or the like. The navigation device 10 can further connect to the municipality server 74 to obtain information relating to any applicable regulations in the area. For instance, a given municipality may require a minimum tire tread depth when snow or ice is present.

Based on this information, the navigation device 10 can select the road(s) that meet optimum safety conditions while tending to the needs of the particular vehicle. For example, if the navigation device 10 determines that the available fuel or electrical charge is likely to run out, it can select a route with gas and/or charging stations. As another example, if the navigation device 10 determines that the vehicle could potentially break down based on its current condition, it can select a route with nearby mechanics or service stations.

In an aspect, the navigation device 10 can utilize elements of system 900 to adjust a route based on sentiment data generated for a user, e.g., by the condition representation component 220 as described above. For example, if sentiment data generated for a passenger of a vehicle indicates that the passenger is unhappy or unwell (e.g., due to motion sickness, etc.), the navigation device 10 can select a navigation route and/or modify an existing navigation route to include one or more roadways with windy conditions in order to enable the passenger to catch a fresh breath of air. The navigation device 10 can determine roadways to select in this manner based on location data corresponding to an area around the vehicle. For instance, a roadway near a beach known to frequently experience windy conditions can be prioritized by the navigation device 10 over an inland roadway with less frequent windy conditions. Also or alternatively, the navigation device 10 could obtain current weather conditions from one or more devices (e.g., the remote server 70 or another Internet-connected device) over a communication network 80, 82. The navigation device could additionally track weather conditions, including wind speed and/or direction, via one or more external sensors associated with the vehicle and/or other nearby vehicles, e.g., nearby vehicles also utilizing a navigation device 10 as shown in FIG. 9. Other techniques for determining wind conditions and selecting a route accordingly could also be used.

In another aspect, a navigation device 10 can leverage system 900 to determine and process dynamic road condition data 340, e.g., as additionally shown by FIG. 8. By way of example, the navigation device 10 can be integrated with real-time image processing capabilities, e.g., via satellite imaging, to observe upcoming road conditions. Road conditions that can be observed in this manner can include, but are not limited to, the following:

1) Wet or icy roads and/or other similar potentially hazardous conditions
2) Road (e.g., asphalt) quality
3) Steep ascents and/or descents
4) Presence of children playing or crowds of people leaving an event near the road, etc.
5) Obstacles, such as fallen trees
6) Rising water bodies, such as rivers
7) High percentages of unsafe drivers, e.g., swerving cars, etc.
8) Pedestrians near a crosswalk or approaching the roadway
9) Wildlife crossings, e.g., deer or other animals approaching the roadway Other conditions could also be used. In the case of pedestrians and/or wildlife approaching the roadway, a risk assessment can be performed based on the direction and speed of approach, historical route data (e.g., common crossing points, etc.), and/or other appropriate data.

FIG. 10 illustrates a method in accordance with certain aspects of this disclosure. While, for purposes of simplicity of explanation, the method is shown and described as a series of acts, it is to be understood and appreciated that this disclosure is not limited by the order of acts, as some acts may occur in different orders and/or concurrently with other acts from that shown and described herein. For example, those skilled in the art will understand and appreciate that methods can alternatively be represented as a series of interrelated states or events, such as in a state diagram. Moreover, not all illustrated acts may be required to implement methods in accordance with certain aspects of this disclosure.

With reference to FIG. 10, a flow diagram of a method 1000 that facilitates sentiment-based navigation in accordance with various aspects described herein is presented. At 1002, a system comprising a processor (e.g., a navigation device 10 comprising a processor 14, and/or a system including such a device) can extract (e.g., by a feature extraction component 210 and/or other components implemented by the processor 14) features of sensor data captured by a sensor (e.g., a sensor 40) associated with a vehicle. The sensor data for which features are extracted at 1002 can be representative of a subject chosen from an occupant (driver, passenger) of the vehicle or an environment in which the vehicle is located.

At 1004, the system can determine (e.g., by a condition representation component 220 and/or other components implemented by the processor 14) sentiment data representative of an emotional condition of the occupant of the vehicle based on an analysis of the features extracted at 1002.

At 1006, the system can generate (e.g., by a routing component 230 and/or other components implemented by the processor 14) a navigation route for the vehicle, e.g., from an origin point to a destination point, based on the sentiment data determined at 1004.

Figure 11:
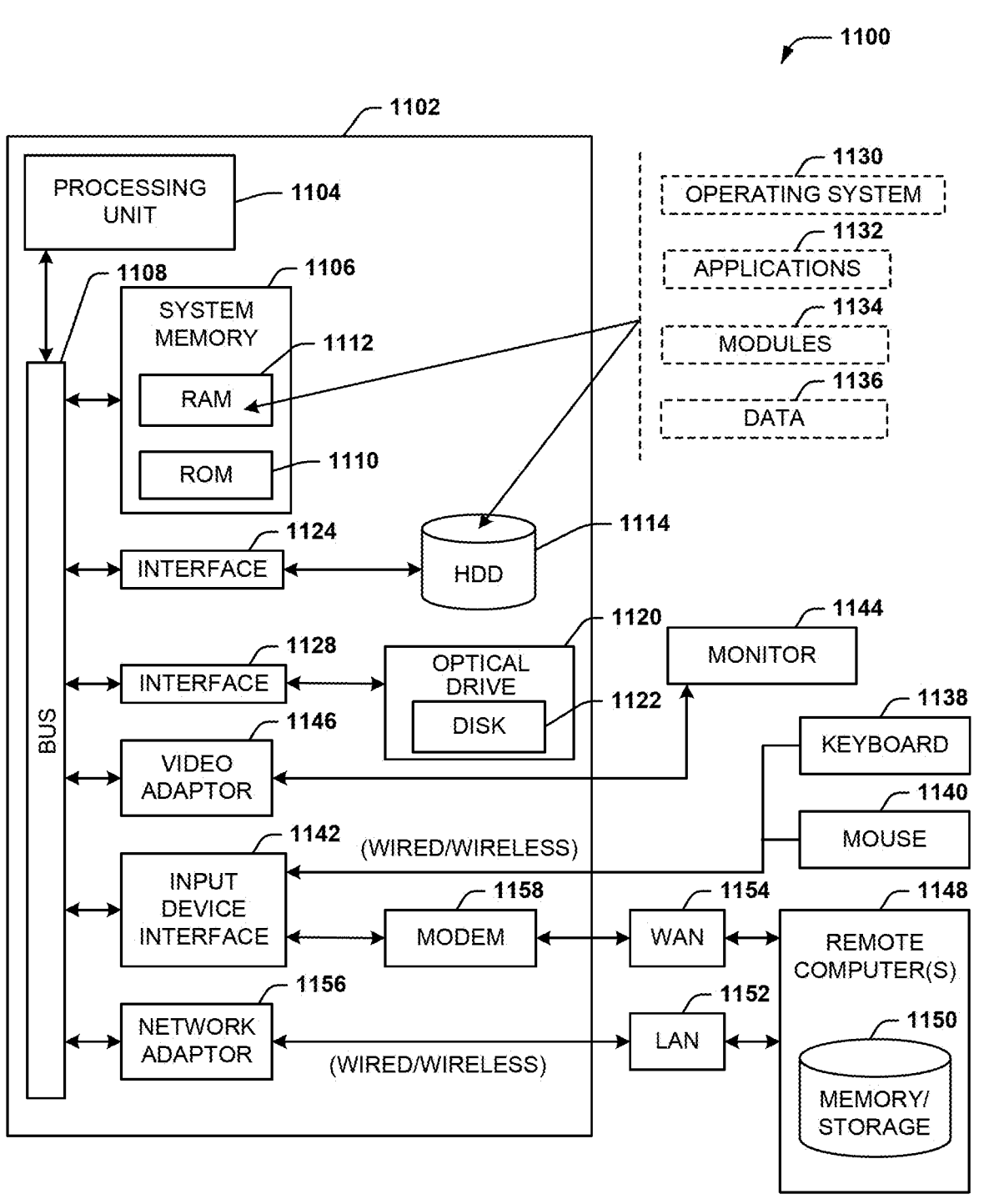
FIG. 11 depicts an example computing environment in which various embodiments described herein can function.

In order to provide additional context for various embodiments described herein, FIG. 11 and the following discussion are intended to provide a brief, general description of a suitable computing environment 1100 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 11, the example environment 1100 for implementing various embodiments of the aspects described herein includes a computer 1102, the computer 1102 including a processing unit 1104, a system memory 1106 and a system bus 1108. The system bus 1108 couples system components including, but not limited to, the system memory 1106 to the processing unit 1104. The processing unit 1104 can be any of various commercially available processors. Dual microprocessors and other multi-processor architectures can also be employed as the processing unit 1104.

The system bus 1108 can be any of several types of bus structure that can further interconnect to a memory bus (with or without a memory controller), a peripheral bus, and a local bus using any of a variety of commercially available bus architectures. The system memory 1106 includes ROM 1110 and RAM 1112. A basic input/output system (BIOS) can be stored in a non-volatile memory such as ROM, erasable programmable read only memory (EPROM), EEPROM, which BIOS contains the basic routines that help to transfer information between elements within the computer 1102, such as during startup. The RAM 1112 can also include a high-speed RAM such as static RAM for caching data.

The computer 1102 further includes an internal hard disk drive (HDD) 1114 and an optical disk drive 1120, (e.g., which can read or write from a CD-ROM disc, a DVD, a BD, etc.). While the internal HDD 1114 is illustrated as located within the computer 1102, the internal HDD 1114 can also be configured for external use in a suitable chassis (not shown). Additionally, while not shown in environment 1100, a solid state drive (SSD) could be used in addition to, or in place of, an HDD 1114. The HDD 1114 and optical disk drive 1120 can be connected to the system bus 1108 by an HDD interface 1124 and an optical drive interface 1128, respectively. The HDD interface 1124 can additionally support external drive implementations via Universal Serial Bus (USB), Institute of Electrical and Electronics Engineers (IEEE) 1394, and/or other interface technologies. Other external drive connection technologies are within contemplation of the embodiments described herein.

The drives and their associated computer-readable storage media provide nonvolatile storage of data, data structures, computer-executable instructions, and so forth. For the computer 1102, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1112, including an operating system 1130, one or more application programs 1132, other program modules 1134 and program data 1136. All or portions of the operating system, applications, modules, and/or data can also be cached in the RAM 1112. The systems and methods described herein can be implemented utilizing various commercially available operating systems or combinations of operating systems.

A user can enter commands and information into the computer 1102 through one or more wired/wireless input devices, e.g., a keyboard 1138 and a pointing device, such as a mouse 1140. Other input devices (not shown) can include a microphone, an infrared (IR) remote control, a joystick, a game pad, a stylus pen, touch screen or the like. These and other input devices are often connected to the processing unit 1104 through an input device interface 1142 that can be coupled to the system bus 1108, but can be connected by other interfaces, such as a parallel port, an IEEE 1394 serial port, a game port, a USB port, an IR interface, a BLU-ETOOTH® interface, etc.

A monitor 1144 or other type of display device can be also connected to the system bus 1108 via an interface, such as a video adapter 1146. In addition to the monitor 1144, a computer typically includes other peripheral output devices (not shown), such as speakers, printers, etc.

The computer 1102 can operate in a networked environment using logical connections via wired and/or wireless communications to one or more remote computers, such as a remote computer(s) 1148. The remote computer(s) 1148 can be a workstation, a server computer, a router, a personal computer, portable computer, microprocessor-based entertainment appliance, a peer device or other common network node, and typically includes many or all of the elements described relative to the computer 1102, although, for purposes of brevity, only a memory/storage device 1150 is illustrated. The logical connections depicted include wired/wireless connectivity to a local area network (LAN) 1152 and/or larger networks, e.g., a wide area network (WAN) 1154. Such LAN and WAN networking environments are commonplace in offices and companies, and facilitate enterprise-wide computer networks, such as intranets, all of which can connect to a global communications network, e.g., the Internet.

When used in a LAN networking environment, the computer 1102 can be connected to the local network 1152 through a wired and/or wireless communication network interface or adapter 1156. The adapter 1156 can facilitate wired or wireless communication to the LAN 1152, which can also include a wireless access point (AP) disposed thereon for communicating with the wireless adapter 1156.

When used in a WAN networking environment, the computer 1102 can include a modem 1158 or can be connected to a communications server on the WAN 1154 or has other means for establishing communications over the WAN 1154, such as by way of the Internet. The modem 1158, which can be internal or external and a wired or wireless device, can be connected to the system bus 1108 via the input device interface 1142. In a networked environment, program modules depicted relative to the computer 1102 or portions thereof, can be stored in the remote memory/storage device 1150. It will be appreciated that the network connections shown are example and other means of establishing a communications link between the computers can be used.

The computer 1102 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This can include Wireless Fidelity (Wi-Fi) and BLUETOOTH® wireless technologies. Thus, the communication can be a predefined structure as with a conventional network or simply an ad hoc communication between at least two devices.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, n, ac, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands, at an 11 Mbps (802.11a) or 54 Mbps (802.11b) data rate, for example or with products that contain both bands (dual band), so the networks can provide real-world performance similar to the basic 10BaseT wired Ethernet networks used in many offices.

The above description includes non-limiting examples of the various embodiments. It is, of course, not possible to describe every conceivable combination of components or methodologies for purposes of describing the disclosed subject matter, and one skilled in the art may recognize that further combinations and permutations of the various embodiments are possible. The disclosed subject matter is intended to embrace all such alterations, modifications, and variations that fall within the spirit and scope of the appended claims.

With regard to the various functions performed by the above described components, devices, circuits, systems, etc., the terms (including a reference to a "means") used to describe such components are intended to also include, unless otherwise indicated, any structure(s) which performs the specified function of the described component (e.g., a functional equivalent), even if not structurally equivalent to the disclosed structure. In addition, while a particular feature of the disclosed subject matter may have been disclosed with respect to only one of several implementations, such feature may be combined with one or more other features of the other implementations as may be desired and advantageous for any given or particular application.

The terms "exemplary" and/or "demonstrative" as used herein are intended to mean serving as an example, instance, or illustration. For the avoidance of doubt, the subject matter disclosed herein is not limited by such examples. In addition, any aspect or design described herein as "exemplary" and/or "demonstrative" is not necessarily to be construed as preferred or advantageous over other aspects or designs, nor is it meant to preclude equivalent structures and techniques known to one skilled in the art. Furthermore, to the extent that the terms "includes," "has," "contains," and other similar words are used in either the detailed description or the claims, such terms are intended to be inclusive—in a manner similar to the term "comprising" as an open transition word—without precluding any additional or other elements.

The term "or" as used herein is intended to mean an inclusive "or" rather than an exclusive "or." For example, the phrase "A or B" is intended to include instances of A, B, and both A and B. Additionally, the articles "a" and "an" as used in this application and the appended claims should generally be construed to mean "one or more" unless either otherwise specified or clear from the context to be directed to a singular form.

The term "set" as employed herein excludes the empty set, i.e., the set with no elements therein. Thus, a "set" in the subject disclosure includes one or more elements or entities. Likewise, the term "group" as utilized herein refers to a collection of one or more entities.

The terms "first," "second," "third," and so forth, as used in the claims, unless otherwise clear by context, is for clarity only and doesn't otherwise indicate or imply any order in time. For instance, "a first determination," "a second determination," and "a third determination," does not indicate or imply that the first determination is to be made before the second determination, or vice versa, etc.

The description of illustrated embodiments of the subject disclosure as provided herein, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as one skilled in the art can recognize. In this regard, while the subject matter has been described herein in connection with various embodiments and corresponding drawings, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

What is claimed is:

1. A method, comprising:

extracting, by a first system comprising a processor, features of sensor data captured by a sensor associated with an autonomous vehicle, wherein the sensor data is representative of a subject selected from a group of subjects comprising an occupant of the autonomous vehicle and an environment in which the autonomous vehicle is located, resulting in extracted features;

determining, by the first system, sentiment data representative of an emotional condition of the occupant of the autonomous vehicle based on an analysis of the extracted features;

generating, by the first system based on image processing data derived from satellite imaging of an area associated with the autonomous vehicle, first partial decision data, wherein the image processing data is distributed among the first system and a second system that is not the first system;

receiving, by the first system from the second system, second partial decision data, the second partial decision data being determined by the second system based on the image processing data; and automatically navigating, by the autonomous vehicle, according to a navigation route, wherein the navigation route is generated based on the sentiment data, the first partial decision data, and the second partial decision data, and wherein the navigation route is generated further based on information relating to presence of line markings on respective roadways associated with the navigation route.

2. The method of claim 1, further comprising:

transmitting, by the first system to a remote server that is distinct from the first system, the sentiment data; and receiving, by the first system from the remote server, route recommendation data generated by the remote server based on the sentiment data;

wherein the navigation route is generated further based on the route recommendation data.

3. The method of claim 1, wherein the sensor comprises an audio sensor, and wherein the sensor data comprises audio data captured by the audio sensor.

4. The method of claim 3, wherein the audio data comprises data representative of speech originating from the occupant of the autonomous vehicle, and wherein the extracting the features of the sensor data comprises determining a property of the speech, the property being selected from a group of properties comprising voice tone and speech content.

5. The method of claim 3, wherein the extracting the features of the sensor data comprises detecting an audio event present in the audio data.

6. The method of claim 3, wherein the extracting the features of the sensor data comprises comparing an amount of audio activity present in the audio data to a defined baseline amount of audio activity, and wherein the determining the sentiment data comprises:

determining an estimated level of distraction associated with the autonomous vehicle based on the comparing; and determining the sentiment data based on the estimated level of distraction.

7. The method of claim 1, wherein the sensor comprises a video sensor, and wherein the sensor data comprises video data captured by the video sensor.

8. The method of claim 7, wherein the video data comprises a depiction of the occupant of the autonomous vehicle, wherein the extracting the features of the sensor data comprises extracting a property of the video data from the depiction of the occupant in the video data, the property being selected from a group of properties comprising movement of the occupant and posture of the occupant, and wherein the determining the sentiment data comprises determining the sentiment data based on the property of the video data.

9. The method of claim 1, further comprising:

obtaining, by the first system, device data from a mobile device associated with the occupant of the autonomous vehicle, and wherein the determining the sentiment data comprises determining the sentiment data further based on the device data.

10. The method of claim 1, wherein the line markings are utilized by the autonomous vehicle for directional guidance.

11. A system of an autonomous vehicle, comprising:

a processor; and a memory that stores executable instructions that, when executed by the processor, facilitate performance of operations, the operations comprising:

extracting features of data captured by a sensor associated with the autonomous vehicle, resulting in extracted data features, wherein the data captured by the sensor is representative of a subject selected from a group of subjects comprising an occupant of the autonomous vehicle and an environment in which the autonomous vehicle is located;

generating condition data representative of an emotional condition of the occupant of the autonomous vehicle by analyzing the extracted data features;

receiving, via a satellite communication system, image processing data derived from satellite image data for an area in which the autonomous vehicle is located, the image processing data being distributed among systems comprising the system and a remote system that is distinct from the system;

generating, based on the image processing data, first partial decision data;

receiving, from the remote system, second partial decision data determined by the remote system based on the image processing data; and automatically navigating the autonomous vehicle according to a navigation route, wherein the navigation route is created based on the condition data, the first partial decision data, and the second partial decision data, and wherein the navigation route is created further based on information relating to a dimension of the autonomous vehicle.

12. The system of claim 11, wherein the operations further comprise:

transmitting the condition data to a server that is distinct from the system; and receiving, from the server, route recommendation data generated by the server based on the condition data, wherein the creating the navigation route is further based on the route recommendation data.

13. The system of claim 11, wherein the sensor comprises an audio sensor, and wherein the data captured by the sensor comprises audio data.

14. The system of claim 13, wherein the audio data comprises speech data representative of speech by the occupant of the autonomous vehicle.

15. The system of claim 14, wherein the extracting the features comprises extracting a feature of the speech that is selected from a group of features comprising voice tone and speech content.

16. The system of claim 13, wherein the extracting the features comprises comparing an amount of audio activity present in the audio data to a defined baseline amount of audio activity, and wherein the operations further comprise:

estimating a level of distraction associated with the autonomous vehicle based on the comparing; and generating the condition data based on the level of distraction.

17. A non-transitory machine-readable medium, comprising executable instructions that, when executed by a processor of a first system of an autonomous vehicle, facilitate performance of operations, the operations comprising:

determining data features that are representative of sensor data captured by a sensor associated with the autonomous vehicle, the sensor data including data representative of a subject selected from a group of subjects comprising an occupant of the autonomous vehicle and an environment in which the autonomous vehicle is located;

generating sentiment data representative of an emotional condition of the occupant of the autonomous vehicle according to the data features;

determining, based on image processing data corresponding to satellite image data depicting an area in which the autonomous vehicle is located, first partial decision data, wherein the image processing data is distributed among systems comprising the first system and a second system that is not the first system;

receiving, from the second system, second partial decision data, the second partial decision data being determined by the second system based on the image processing data; and automatically navigating the autonomous vehicle according to route data, wherein the route data is representative of a navigation route for the autonomous vehicle and is based on the sentiment data, the first partial decision data, and the second partial decision data, and wherein the route data representative of the navigation route is further based on information relating to a speed capability of the autonomous vehicle.

18. The non-transitory machine-readable medium of claim 17, wherein the operations further comprise:

transmitting the sentiment data to a remote server via a communication network; and receiving, from the remote server, route recommendation data generated by the remote server based on the sentiment data, wherein the route data is further based on the route recommendation data.

19. The non-transitory machine-readable medium of claim 17, wherein the sensor comprises an audio sensor, and wherein the sensor data comprises audio data captured by the audio sensor.

20. The non-transitory machine-readable medium of claim 19, wherein the audio data comprises speech data representative of speech originating from the occupant of the autonomous vehicle, and wherein the operations further comprise:

extracting, as a data feature of the data features, a property of the speech that is selected from a group of properties comprising voice tone and speech content.

\*    \*    \*    \*    \*